United States Patent [19]

Nehne et al.

[11] Patent Number: 5,874,470
[45] Date of Patent: Feb. 23, 1999

[54] ISOTONIC FAT EMULSION CONTAINING OMEGA-3-FATTY ACIDS AND USE THEREOF

[75] Inventors: Joerg Nehne, Guxhagen; Michael Boll, Melsungen, both of Germany

[73] Assignee: B. Braun Melsungen AG, Germany

[21] Appl. No.: 301,185

[22] Filed: Sep. 6, 1994

Related U.S. Application Data

[63] Continuation of Ser. No. 980,105, Nov. 23, 1992, abandoned, which is a continuation of Ser. No. 827,505, Jan. 27, 1992, abandoned, which is a continuation of Ser. No. 693,045, Apr. 29, 1991, abandoned, which is a continuation of Ser. No. 559,399, Jul. 26, 1990, abandoned, which is a continuation of Ser. No. 254,497, Oct. 6, 1988, abandoned.

[30] Foreign Application Priority Data

Oct. 9, 1987 [DE] Germany .............................. 3734147.2

[51] Int. Cl.$^6$ ........................ A61K 31/22; A61K 31/355; A61K 31/23
[52] U.S. Cl. .......................... 514/560; 514/458; 514/549; 514/552
[58] Field of Search .................................. 514/552, 560, 514/458, 549

[56] References Cited

U.S. PATENT DOCUMENTS

| | | | |
|---|---|---|---|
| 4,526,902 | 7/1985 | Rubin ....................................... | 514/560 |
| 4,703,062 | 10/1987 | Blackburn et al. ...................... | 514/552 |
| 4,871,768 | 10/1989 | Bistrian et al. .......................... | 514/547 |
| 4,920,098 | 4/1990 | Cotter et al. ............................. | 514/560 |
| 5,034,414 | 7/1991 | Wakabayashi et al. ................. | 514/549 |
| 5,574,065 | 11/1996 | Trimbo .................................... | 514/546 |

FOREIGN PATENT DOCUMENTS

| | | |
|---|---|---|
| A0145873 | 12/1980 | European Pat. Off. . |
| Sho58-230918 | 12/1978 | Japan . |

OTHER PUBLICATIONS

Marra et al., "Dexamethasone Blocks Arachidonate Biosynthesis in Isolated Hepatocytes and Cultured Hepatoma Cells" *lipids*, 21:212–219 (1986).
Gómez Dumm et al., "Effect of epinephrine on the oxidative desaturation of fatty acids in the rat" *J. Lipid Res.*, 17:616–621 (1976).
Gómez Dumm et al., "Effect of Catecholamines and β–Blockers on Linoleic Acid Desaturation Activity" *Lipids*, 13:649–652 (1978).
Gómez Dumm et al., "Effect of glucocorticoids on the oxidative desaturation of fatty acids by rat liver microsomes" *J. Lipid Res.*, 20:834–839 (1979).
Mercuri et al., *Biochim. Biophys. Acta*, 116:409–411 (1966).
Hansen et al., "Influence of Diet on Blood Serum Lipids in Pregnant Women and Newborn Infants" *American Jounral of Clinical Nutrition*, 15:11–19 (1964).
Mendy et al., "Étude de la Composition en acides Gras Polydésaturés des Lipides Sériques de Nourrissons Soumis a des Régimes Différents" *Ann. Nutr. Alim.*, 22:267–285 (1968).
Mendy et al., "Facts About Linoleic Acid Metabloic Fate During Pufa Rich Diets in Human" *Lipid metabolism and its pathology*, M.J. Halpern, editor, 213–223 (1986).
Blond et al., "Désaturation comparée des acides linoléique et dihomo–γ–linolénique par des homogénats de foie humain in vitro" *C.R. Acad. Sc. Paris*, 292:911–914 (1981).
Rivers et al., "Inability of the cat to desaturate essential fatty acids" *Nature*, 258:171–173 (1975).
Iacono et al., "Change in Plasma and Erythrocyte Lipids During Short–Term Administration of Intravenous Fat Emulsion and Its Subfractions" *American Journal of Clinical Nutrition*, 16:165–172 (1965).
Breton et al., "Interet des Acides Gras Polydesatures Essentials Dans la Pratique Quotidinne de la Medecine D'Enfants" *La Revue de Pediatrie*, 1:43–55 (1966).
Nouvelot et al., "Etude métabolique de trois émulsions lipidiques utiliséees dans l'alimentation parentérale" *Nutr. Metabol.* 19:307–317 (1975).
Agradi et al., "Influence of Short Term Dietary Supplementaion O Different Lipids on Aggregation and Arachidonic Acid Metabolism in Rabbit Platelets" *Prostaglandins*, 16:973–984 (1978).
Galli et al., "Differential Effects of Dietary Fatty Acids on the Accumlation of Arachidonic Acid and Its Metabolic Coinversion through the Cyclooxygenase and Lipoxygenase in Platelets and Vascular Tissue" *Lipids*, 16:165–172 (1981).
Friedman et al., "Essential Fatty Acids and the Major Urinary Metabolites of the E Prostaglandins in Thriving Neonates and in Infants Receiving Parenteral Fat Emulsions" *Pediat. Res.*, 13:932–936 (1979).

*Primary Examiner*—Raymond Henley, III
*Attorney, Agent, or Firm*—Christie, Parker & Hale, LLP

[57] ABSTRACT

Isotonic fat emulsions are provided which incorporate ω-3-fatty acids, ω-6-fatty acids, and medium-chain triglycerides. The emulsions are useful for parenteral application in post-aggression metabolism, in cases of chronic inflammatory diseases, and in neonatology and pediatrics. Due to the combination of ω-3-fatty acids and/or their physiologically acceptable esters with medium-chain-triglycerides, the medium-chain triglycerides are preferred to be oxidized in the organism, and the ω-3 fatty acids are protected from rapid oxidation, so that they are available to a higher extent for the formation of triply unsaturated eicosanoids. Furthermore, a liver protective effect is attained by the combination.

3 Claims, 7 Drawing Sheets

ISOTONIC FAT EMULSION CONTAINING OMEGA-3-FATTY ACIDS AND USE THEREOF

This is a continuation of application Ser. No. 07/980,105, filed Nov. 23, 1992, now abandoned, which is a continuation of U.S. Ser. No. 07/827,505, filed Jan. 27, 1992 now abandoned, which is a continuation of Ser. No. 07/693,045, filed Apr. 29, 1991, now abandoned, which is a continuation of U.S. Ser. No. 07/559,399filed Jul. 26, 1990, now abandoned, which is a continuation of Ser. No. 07/254,497, filed Oct. 6, 1998, now abandoned.

The present invention relates to isotonic fat emulsions containing ω-3-fatty acids for parenteral application and the use thereof in post-aggression metabolism or in the treatment of chronic inflammatory diseases.

Fatty emulsions have the function to introduce fat into the organism in an intravenously compatible administration form, if a regular (enteral) alimentation is not possible or is contra-indicated for medical reasons. The medium-chain triglycerides (MCT) or long-chain triglycerides (LCT) administered with the fat emulsions serve as energy source and as source for essential fatty acids, the latter being applicable only to the case of the long-chain triglycerides as far as these contain multiply unsaturated fatty acids.

Patients in a normal condition of nutrition mostly have sufficient fat reserve supplies to meet their energy and essential fatty acid requirements from their own supplies during short periods of zero-diet. However, serious and long-lasting diseases are accompanied with an increased need for essential fatty acids as well as an enhanced demand for energy and an indication of a parenteral alimentation for extended periods of time. Thus, they constitute the main field of application for intravenous fat emulsions. Carbohydrate solutions, apart from the fact that they fail to provide essential fatty acids, are not suitable as the sole source of energy in the case of serious illness, because the utilization thereof in the post-aggression metabolism is impaired. In contrast thereto, fats, whether of endogenous or exogenous origin, are preferred to be utilized in the post-aggression metabolism. This observation underscores the basic suitability of lipid emulsions for parenteral alimentation and for the substitution of essential fatty acids in the cases of serious diseases and the situations of metabolism associated therewith.

However, under qualitative aspects hitherto the practice of intravenous fat supply has been unsatisfactory. The fat emulsions presently available are prepared from oils of vegetable origin (soybean oil or safflower oil); in some cases they also contain medium-chain triglycerides.

The oils of soybean and of the safflower thistle are characterized by a high proportion of multiply unsaturated fatty acids of the ω-6 series (in the main: linoleic acid 18:2ω-6), while their contents of ω-3-fatty acids is low. In soybean oil the proportion of ω-3-fatty acids based on the total contents of fatty acids is about 7%, and in the safflower oil it is about 1%. In both cases the ω-3-fatty acids are virtually present only as α-linolenic acid (18:3ω-3). Medium-chain triglycerides do not contain any unsaturated fatty acids at all and, thus, they contain neither ω-6- nor ω-3-fatty acids.

The classification of unsaturated fatty acids in those of the ω-3- or ω-6 series is based on features of the chemical structure, and more specifically on the positions of the unsaturated bonds in the fatty acid molecule. The human organism is not able by itself to produce multiply unsaturated fatty acids which are essential therefor, i.e. a supply of which by enteral or parenteral food is indispensably necessary. However, it is able to synthesize longer-chain unsaturated fatty acids from shorter-chain unsaturated fatty acids, such as, e.g., in the ω-6 series arachidonic acid (20:4ω-6) from linoleic acid and in the ω-3 series eicosapentaenoic acid (20:5ω-3) from α-linolenic acid (cf. Scheme 1). A formation of ω-6-fatty acids from precursors of the ω-3 series or vice versa is not possible.

The ω-3- as well as the ω-6-fatty acids are essential for human, however, with different values.

Conventional fat emulsions due to the high linoleic acid are well suited to meet the requirements with respect to the ω-6-fatty acids. With respect to the ω-3-fatty acids in the conventional fat emulsions, things look quite different: Here the content of α-linolenic acid is a priori low, and in metabolism linoleic acid and linolenic acid will compete for the desaturating and elongating enzymes. Therefore, a desaturation of α-linolenic acid in the presence of higher amounts of linoleic acid as supplied with the fat emulsions hitherto will take place only to an extremely Scheme No. 1 low extent. Therefore, under a biological aspect the ω-3-fatty acids, in spite of their proportion of 7% of the total fatty acids of soybean oil, are nearly inactive. In contrast thereto the formation of the arachidonic acid (wherefrom the biological activities of the ω-6-fatty acids are derived) from the linoleic acid contained in soybean oil or safflower oil proceeds mostly unaffected.

The biological importance of the essential fatty acids consists in that they are precursors of prostaglandins, thromboxanes and leucotrienes. These substances collectively designated as eicosanoids act in a similar manner as hormones and influence numerous functions of the organism such as vascular tonus, vascular permeability, pulmonary vascular resistance, thrombus formation, blood pressure regulation, inflammatory-allergic reactions etc. The eicosanoids are nearly ubiquitously formed in the body from locally released membrane fatty acids, eicosanoids with a triply unsaturated side-chain from eicosapentaenoic acid, and eicosanoids with a doubly unsaturated side-chain from arachidonic acid (see Scheme No. 1). Depending on their origin from one of these fatty acids, the eicosanoids have different biological properties (see hereinbelow).

As the precursor-fatty acids or their precursors, respectively, (α-linolenic acid for the ω-3-fatty acids; linoleic acid for the ω-6-fatty acids) themselves cannot be formed in the human organism, the occurrence thereof in the body depends on the supply with the food or—upon parenteral alimentation—on the intravenous supply. In the so-called "Western nutrition" as common in Europe and America—and—as has already been set forth—in the fat emulsions hitherto used for parenteral alimentation—the ω-6-fatty acids do by far prevail and, hence, in the eicosanoid-mediated effects doubly unsaturated prostaglandins and thromboxans play the main role. Different is the situation in populations traditionally living on a fish diet such as the Eskimos (Inuits, Aleuts) and Japanese. Their diet contains a high proportion of ω-3-fatty acids which are the precursors for triply unsaturated eicosanoids.

The biological effects of triply unsaturated eicosanoids which include $PGI_3$, $PGE_3$ and $TXA_3$ as the most important representatives in part support those of the doubly unsaturated eicosanoids (e.g. $PGI_2$, $PGE_2$ and $TXA_2$) and in part inhibit these. Thus, $PGI_3$ has a vasodilative and aggregation-inhibitive action as strong as that of $PGI_2$. However, in contrast thereto, the vasoconstrictive and aggregation-promoting effect of $TXA_2$ is competitively inhibited by $TXA_3$ which is inactive itself. In a similar manner $PGE_3$ can inhibit the bronchoconstrictive edema-promoting and immunosuppressive effects of $PGE_2$.

Similar interactions occur between the leucotrienes produced by lipoxygenation from arachidonic acid (e.g. $LTB_4$) and those derived from eicosapentaenoic acid (e.g. $LTB_5$). Thus, $LTB_4$ is a highly potent inflammation mediator, whereas $LTB_5$ only shows low effectivity and, consequently, reduces the effect of $LTB_4$.

Thus, while among the doubly unsaturated eicosanoids there occur vasoconstrictive pro-aggregatory as well as vasodilative anti-aggregatory properties, in the triply unsaturated eicosanoids the vasodilative and aggregation-inhibitive properties and inhibitory effects on certain doubly unsaturated eicosanoids prevail. In populations with high consumption of a diet rich in ω-3-fatty acids such as the Eskimos and Japanese already mentioned, therefrom ensues, in comparison to populations on "Western" diet, a conspicuously low rate of arteriosclerotic vascular diseases, besides other particularities. Of even higher significance than in persons having a "healthy metabolism" are the prostaglandin effects in stress metabolism: Namely, under normal conditions there is an equilibrium state between the partially antagonistic effects of doubly unsaturated eicosanoids.

However, under the influence of stress factors such as histamine, bradykinin and complement factors this equilibrium is shifted to the side of the potentially disadvantageous (vasoconstrictive, pro-aggregatory, pro-inflammatory) eicosanoid effects.

This constellation is increasedly found in seriously ill patients and just those requiring a parenteral alimentation with fat emulsion: patients in post-aggression metabolism after surgery and multiple traumata, in septic patients and patients under artificial respiration. For such factors the predominance of stress factors is typical, which cause the equilibrium to be shifted to the side of the disadvantageous effects of doubly unsaturated eicosanoids, and the undesirable effects are still promoted by the administration of fat emulsions having a high content of linoleic acid. Even with seriously ill patients who within the regimen of their parenteral alimentation do not receive fat emulsions disadvantageous effects mediated by doubly unsaturated eicosanoids may possibly occur. Due to the diet taken prior to the disease also for those patients, and particularly after preceding "Western" nutrition, a high proportion of ω-6-fatty acids in the membrane fatty acids is to be expected and, thus, so are the corresponding eicosanoid effects.

Triply unsaturated eicosanoids which reduce the disadvantageous effects provided by doubly unsaturated eicosanoids mostly cannot be produced by the organisms of the respective patients to the extent required, because the contents of ω-3-fatty acids in the membrane fatty acids upon preceding "Western" diet is too low and in the instant situation an enteral supply of eicosapentaenoic acid is not feasible. The fat emulsions and components thereof so far used for by-passing the period of food deprivation either do not contain ω-3-fatty acids as in the case of safflower oil and medium-chain triglycerides, or the formation of eicosapentaenoic acid from α-linolenic acid is inhibited by the simultaneously high linoleic acid content as in the case of soybean oil.

By way of experiments it could be shown by J. W. Alexander, Arch. Surg. Vol. 121, Aug. 1986, p. 966 et seq., that animals suffering from burn trauma (30% of body area) under a diet rich in linoleic acid (rich in ω-6-fatty acids) had a significantly shorter survival time, a higher metabolic rate (corresponding to an enhanced stress metabolism) and an inferior immunocompetence than animals under a diet rich in fish oil (rich in ω-3-fatty acids) comparison diet. By administration of Indomethacin, a blocker of the prostaglandin synthesis, the disadvantageous effects of the diet rich in linoleic acid could in part be reversed and similar results could be obtained as in the fish oil group. Therefrom it is evident that prostaglandins from the ω-6-fatty acids or linoleic acid series are directly responsible for the bad prognosis of the animals of the respective groups.

However, in clinical practice the inhibition by Indomethacin of the prostaglandin synthesis starting from arachidonic acid involves problems, since thereby only eicosanoids of the cyclooxygenase route are blocked and instead a transfer is initiated to the lipoxygenase route which is associated with an enhanced edema formation and an increased ARDS risk, as has been described by W. Seeger et al. and H. Wolf et al. in Klin. Wochenschr. 1981; 59:459 et seq. and 463 et seq., respectively.

Thus, in accordance with the state of the art as described up to here, there is demand for a fat emulsion for the parenteral administration in the post-aggression metabolism, which emulsion contains lesser precursors of doubly unsaturated eicosanoids and of quadruply unsaturated leucotrienes, i.e. less linoleic acid in practice, but instead contains precursors of triply unsaturated eicosanoids and quintuply unsaturated leucotrienes, i.e. ω-3-fatty acids, and preferably eicosapentaenoic acid. Whether the respective fat emulsion contains only ω-3-fatty acids or a combination of ω-3- and ω-6-fatty acids will depend on whether acutely influencing the prostaglandin effects by ω-3-fatty acids or an application over an extended period of time within the regimen of a parenteral alimentation is the primary object. In the latter case, ω-6-fatty acids (linoleic acid) because of their essentiality cannot be omitted.

Therefore, on the ground of this knowledge it was proposed to emulsify ω-3-fatty acids or esters thereof (e.g. a purified fish oil) alone or in combination with a vegetable oil and to formulate the obtained emulsion into a dosage form suitable for intravenous infusion or an other form of administration.

The U.S. Pat. No. 4,526,902 describes mixtures comprising from 25 to 75% by weight of eicosapentaenoic acid and an ω-6-fatty acid which is enterally used as a component of pharmaceutics or fat-containing foods such as butter or the like.

In the EP 0 120 169 B1 there have been described synthetic triglycerides which may have, on the central carbon atom of the glycerol molecule, a multiply unsaturated fatty acid, and preferably eicosapentaenoic acid. The glycerides thus produced may be used as foods, food supplements or drugs for therapeutic nutrition.

The EP-A-0 145 873 discloses a transfusion emulsion for food supplementing which contains a fat proportion of from 5 to 20% w./v., the balance being water, wherein the fat phase consists of from 10 to 50% w./v. of α-linolenic acid or its glycerol or ethyl ester and from 50 to 90% w./v. of a vegetable oil containing a ω-6-fatty acid, such as safflower oil or soybean oil, respectively.

The Japanese published unexamined patent application Sho-58-230918 describes an emulsion containing eicosapentaenoic acid for oral and non-oral use. Said emulsion contains from 1 to 40% w./v. of eicosapentaenoic acid or, preferably, its methyl or ethyl ester, from 1 to 30% w./v. of a vegetable oil, and preferably soybean oil, from 0.01 to 30% w./v. of α-tocopherol and, as emulsifiers, from 0.1 to 5% w./v. of a phospholipid, preferably from egg yolk and/or soybean, and from 0.1 to 10% w./v. of a non-ionic synthetic emulsifier.

The German Offenlegungsschrift 34 09 793 discloses a liquid emulsion for transfusion having an antithrombic and antiarteriosclerotic activity which emulsion may serve to supplement a diet. It consists of, in addition to water, from 5 to 20% w./v. of eicosapentaenoic acid, docosahexaenoic acid or the esters thereof, and preferably it is a purified fish oil such as sardine oil. It further contains from 1 to 19% w./v. of a vegetable oil, and preferably soybean oil and/or safflower oil, and from 1 to 2% w./v. of a phospholipid emulsifier, preferably derived from egg yolk or soybean. This emulsion may be admixed with α-tocopherol as antioxidant.

However, in the quoted papers it has been left unconsidered that under the conditions mentioned ω-3-fatty acids to the largest part thereof are utilized in energy metabolism, i.e. they are oxidized. Thereby they are prevented from fulfilling other functions such as, e.g., the formation of eicosanoids. In post-aggression metabolism, the oxidation of triglycerides for energy production—as has already been mentioned—is even particularly high. Thus, the method of a direct "unprotected" supply of fat emulsions containing ω-3-fatty acids is at least uneconomical—if feasible at all, as considerable doubts must exist as to the relative amounts having been oxidized and being available for eicosanoid formation, respectively. With other words, from a dosage administered under these conditions no defined effect can be expected, since it cannot be anticipated at which percentage the ω-3-fatty acids are otherwise utilized.

Thus, in extension of the object described above, it is to be ensured that the ω-3-fatty acids administered for antagonizing the undesired effects provided by doubly unsaturated eicosanoids and quadruply unsaturated leucotrienes will be available as fully as possible to serve this purpose.

SUMMARY OF THE INVENTION

Surprisingly, it was now found that said problem can be solved by way of administration of a combination of ω-3-fatty acids a fish oil containing ω-3-fatty acids, or a fish oil fraction, respectively, with medium-chain triglycerides. Namely, in detail it was found that the fatty acids of purified fish oil, if the latter were processed together with medium-chain triglycerides into an emulsion and were intravenously infused, effused less readily effused from the intravasal space and were oxidized to a significantly lesser extent than upon sole administration of a fish oil emulsion.

It was further found that the combined administration of purified fish oil containing -3-fatty acids or of a respective fish oil fraction with medium-chain triglycerides has an advantageous liver-protective effect. Thus, rats exhibited marked fat inclusions in the liver, and more specifically in the Kupffer cells, upon a long-term administration of an emulsion containing only triglycerides from fish oil. If, however, the rats were treated with the same amounts of triglycerides from fish oil in a combined emulsion containing medium-chain triglycerides, then virtually no signs were found any more of a fat infiltration in the liver.

BRIEF DESCRIPTION OF THE DRAWINGS

The file of this patent contains at least one color drawing (photograph). Copies of this patent with color drawings will be provided by the Patent and Trademark Office upon request and payment of the necessary fee.

These and other features, aspects, and advantages of the present invention will be more fully understood when considered with respect to the following detailed description, appended claims, and accompanying drawings, wherein:

DETAILED DESCRIPTION

The invention relates to an isotonic fat emulsion for parenteral application, the emulsion containing ω-3-fatty acids, and more specifically eicosapentaenoic acid (EPA) or its physiologically acceptable esters as components of the fat phase, which is characterized in that the fat emulsion contains these ω-3-fatty acids or esters in the pure state or as component(s) of fish oils, medium-chain triglycerides (MCT), at least one physiologically acceptable emulsifier, optionally at least one vegetable oil providing ω-6-fatty acids, α-tocopherol or physiologically acceptable α-tocopherol esters, and conventional additives or auxiliary materials, whereby the ratio of EPA or its physiologically acceptable esters and MCT is between 1:9 and 3:5, the total fat contents is between 5 and 30%, the emulsifier contents is between 5 and 12% (based on the fat contents), and the contents of vegetable oil providing ω-6-fatty acids is between 0 and 30% (based on the fat contents).

According to the invention, ω-3-fatty acids such as, for example, docosahexaenoic acid, eicosapentaenoic acid and the esters thereof, and more specifically eicosapentaenoic acid (EPA) and its physiologically acceptable esters can be used either in the pure state or as component(s) of fish oil.

Suitable compounds are, besides EPA itself, the pharmacologically acceptable lower alkyl esters and glycerol esters thereof. Preferred are the EPA ethyl ester and EPA glycerol ester.

Suitable fish oils, for example, are those as commercially recovered to an important degree from cold water fish. Preferred are highly purified fish oil concentrates which are recovered, for example, from mackerel, sardine, herring or salmon, these having an EPA contents of from 20 to 40%, and preferably at least of 26% (based on the fatty acid methyl esters of the fish oil concentrate).

The medium-chain triglycerides employed according to the invention are those consisting of at least 90% of glycerides of caprylic and capric acids. The ratio of EPA and its physiologically acceptable esters to the medium-chain triglycerides should be between 1:9 and 3:5.

The emulsifiers employed are physiologically compatible emulsifiers such as phospholipids of animal and vegetable origin, and more particularly those derived from hen's egg yolk or soybean.

The emulsifier contents are from 5 to 12% (based on the fat contents), and the total fat contents of the fat emulsion are between 5 and 30%.

In addition to the components mainly containing ω-3-fatty acids, a vegetable oil providing an ω-6-fatty acid may be employed as an optional component. From among these, safflower oil and/or soybean oil are preferred to be used, the contents of said vegetable oils being between 0 and 30%, based on the fat contents.

As emulsifying auxiliary materials there may be further employed sodium salts of long-chain fatty acids (preferably in a concentration of from 0.005 to 0.1% by weight, based on the total emulsion) and/or cholesterol or cholesterol esters (preferably in a concentration of from 0.005 to 0.1% by weight, based on the total emulsion).

The fat emulsion is preferred to have a pH value within the range of from 6 to 9.

Eventually, the fat emulsion may contain, as an antioxidant and, thus, for protection from peroxide formation, α-tocopherol or α-tocopherol ester in an amount of from 10 to 1000 mg, based on 100 g of fat, more particularly so, if ω-3-fatty acids, and more specifically EPA and its esters, are used in the pure state.

The present invention further relates to a process for preparing the above-mentioned fat emulsions.

The combination of fish oil with medium-chain triglycerides in the described manner involves a retarding effect on the clearance and oxidation of the fatty acids from fish oil. Thereby, on the one hand, the residence time of the ω-3-fatty acids in the circulation is increased and virtually a depot effect is achieved; on the other hand, the nutritive (oxidative) utilization of the ω-3-fatty acids is slowed down in favour of the enhanced incorporation in membrane fatty acids and membrane phospholipids and an increased availability for the synthesis of eicosanoids.

Besides, the combination of fish oil with medium-chain triglycerides protects the liver from fat infiltration observed upon sole administration of purified fish oil, fish oil fractions containing ω-3-fatty acids or esters of ω-3-fatty acids. These protective effects are not obtained, if fish oil is mixed with vegetable oil in the place of MCT oil and processed in the described manner to form an emulsion. Thus, the ω-3-fatty acids-sparing and liver-protective effect is a consequence of the particular combination with medium-chain triglycerides.

The invention further relates to a fat emulsion for use in post-aggression metabolism, and more specifically after surgery and multiple traumata, in cases of burns, infections and of pending and manifest lung failure, and for use in treating of chronic inflammatory diseases. The fat emulsion according to the invention may be used also in neonatology and pediatrics.

The percentages each in the descriptions and in the claims, unless otherwise stated, are those given in grams per 100 ml of solution.

The invention is further illustrated by the following examples.

EXAMPLE 1

A mixture of 600 g of a highly purified fish oil, 1,400 g of MCT, 2 g of cholesterol acetate, 120 g of purified egg phospholipids and 2 g of sodium stearate is finely dispersed by using an Ultra-Turrax. The mixture while stirred is filled up to a total of 10 liters with water for injectables containing 250 g of glycerol and 5 mmol of NaOH. This crude pre-emulsion is homogenized in a high pressure homogenator under a pressure of 392 bar (400 kg/cm$^2$). The product is bottled in glass bottles of suitable quality and heat-sterilized according to generally known methods. The particles of the sterile and pyrogen-free emulsion are smaller than 1 μm.

EXAMPLE 2

A mixture of 400 g of a highly purified fish oil, 600 g of MCT, 90 g of purified egg phospholipids and 4 g of sodium stearate is dispersed as described in Example 1 and, after refilling with water for injectables (containing 250 g of glycerol) to a total of 10 liters, homogenized, bottled and sterilized.

The emulsion droplets are smaller than 1 μm.

EXAMPLE 3

A mixture of 300 g of eicosapentaenoic acid ethyl ester, 700 g of MCT, 60 g of purified egg phospholipids, 500 mg of α-tocopherol and 2 g of sodium stearate is dispersed as described in Example 1 and, after refilling with water for injectables (containing 125 g of glycerol) to a total of 5 liters, homogenized, bottled and sterilized.

The emulsion droplets are smaller than 1 μm.

EXAMPLE 4

A mixture of 300 g of a purified fish oil, 600 g of purified safflower oil, 1,100 g of MCT, 120 g of purified egg phospholipids, 200 mg of α-tocopherol acetate and 3.5 g of sodium stearate is dispersed as described in Example 1. After refilling with water (containing 250 g of glycerol) to a total of 10 liters, the mixture is homogenized, bottled and sterilized. The emulsion droplets are smaller than 1 μm.

EXAMPLE 5

A mixture of 200 g of a highly purified fish oil, 300 g of MCT and 90 g of purified egg phospholipids is dispersed as described in Example 1 and, after refilling with water for injectables (containing 250 g of glycerol) to a total of 10 liters, homogenized. The pH value is adjusted with NaOH to pH 8.0 to 8.5, and the mixture is bottled and sterilized. The resulting emulsion comprises fat droplets which are smaller than 1 μm.

EXAMPLE 6

A mixture of 250 g of a highly purified fish oil, 500 g of MCT and 60 g of purified soybean phospholipids is dispersed as described in Example 1 and, after refilling with water for injectables (containing 125 g of glycerol) to a total of 5 liters, homogenized. The pH value is adjusted with NaOH to pH 8.0 to 8.5, and the mixture is bottled and sterilized. The particles of this emulsion are smaller than 1 μm.

EXAMPLE 7

One hundred grams of eicosapentaenoic acid are dissolved in 900 g of MCT. Upon addition of 90 g of purified egg phospholipids, 200 mg of α-tocopherol, 3 g of cholesterol acetate and 3 g of sodium stearate is dispersed as described in Example 1 and, after refilling with water for injectables (containing 250 g of glycerol) to a total of 10 liters, homogenized. The pH value is adjusted with NaOH to pH 8.0 to 8.5, and the mixture is bottled and sterilized. The resulting emulsion droplets are smaller than 1 μm.

EXAMPLE 8

A mixture of 200 g of eicosapentaenoic acid ethyl ester, 1,600 g of MCT, 200 g of purified soybean oil, 150 g of purified egg phospholipids, 500 mg of α-tocopherol and 4 g of sodium stearate is dispersed as described in Example 1 and, after refilling with water for injectables (containing 250 g of glycerol) to a total of 10 liters, homogenized, bottled and sterilized. The emulsion droplets are smaller than 1 μm.

EXAMPLE 9

A mixture of 150 g of eicosapentaenoic acid ethyl ester, 1,350 g of MCT, 650 mg of α-tocopherol, 1.5 g of cholesterol acetate, 4 g of sodium stearate and 90 g of purified egg phospholipids is dispersed as described in Example 1 and, after refilling with water for injectables (containing 125 g of glycerol) to a total of 5 liters, homogenized, bottled and sterilized. The particles of the emulsion are smaller than 1 μm.

EXAMPLE 10

A mixture of 300 g of a highly purified fish oil, 700 g of MCT, 80 g of purified soybean phospholipids, 100 mg of α-tocopherol acetate and 3 g sodium stearate is dispersed as described in Example 1 and, after refilling with water for injectables (containing 250 g of glycerol) to a total of 10 liters, homogenized, bottled and sterilized. The emulsion droplets are smaller than 1 μm.

The action of the emulsion is illustrated by the following examples.

Application Example 1

The clearance in dogs of fish oil-containing emulsions was investigated in response to the presence of medium-chain triglycerides in the emulsions. To this end, 6 Beagle dogs fasted overnight were administered an intravenous infusion of a 10% emulsion made up from highly purified fish oil and MCT oil in a ratio of 40:60 according to the preparative EXAMPLE 12. The infusion rate was 1.5 ml per kilogram of body weight and per hour (≈60 mg of fish oil/kg of body weight·hour). As the control, three days later the same animals, again fasted overnight, were intravenously infused with a 10% emulsion containing only fish oil at a rate of 0.6 ml per kilogram of body weight and per hour (≈60 mg of fish oil/kg of body weight·hour). In both cases the infusion period was 3 hours. During the infusions and some time after, blood samples were taken, and the total level of fatty acids in serum was analyzed by gas chromatography.

Figure 1:
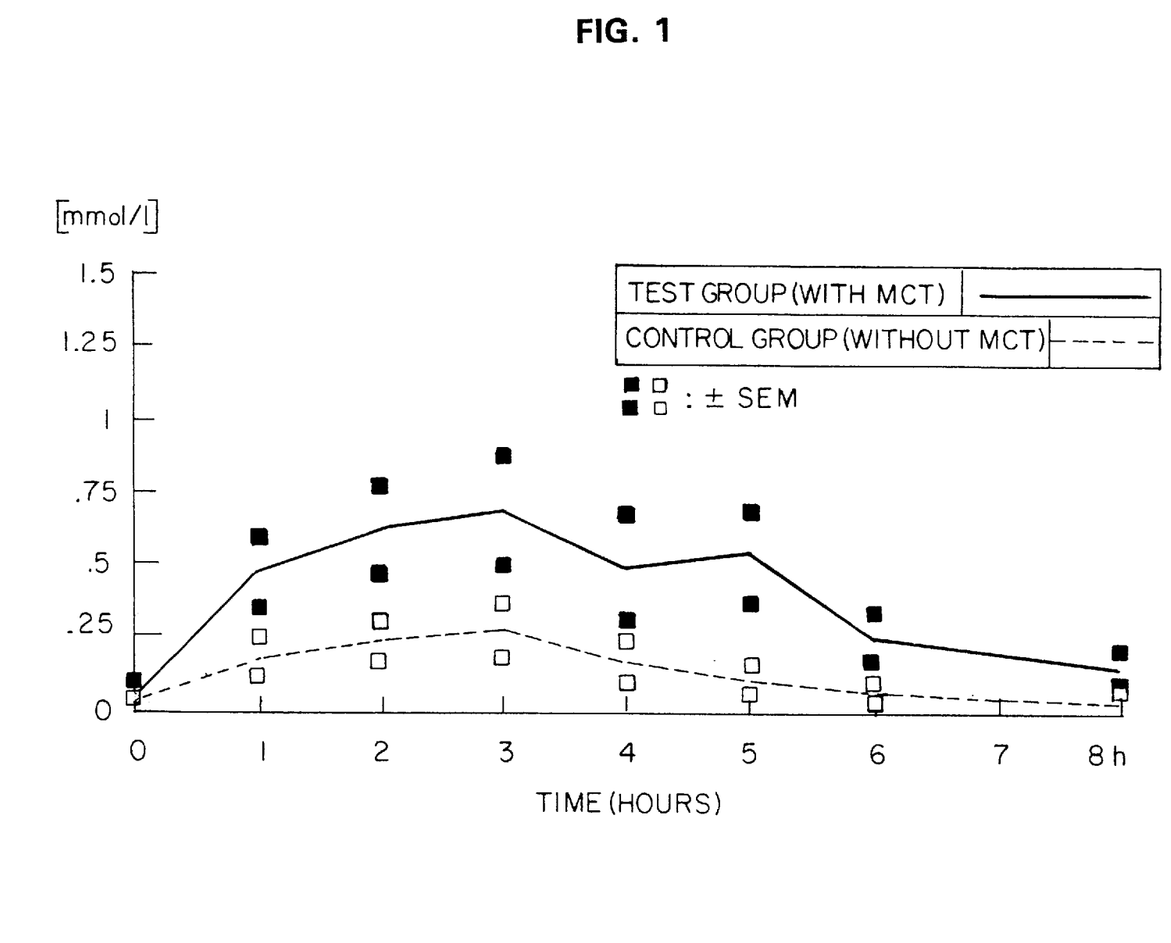
FIG. 1 shows a plot of the concentration of eicosapentaenoic acid versus time during and after infusion into test animals.

FIG. 1 shows a plot of the concentration of eicosapentaenoic acid vs. time during and after infusion for both groups.

In spite of the same dose of fish oil in both groups, in the group with MCT contents the serum concentrations of eicosapentaenoic acid rose to a higher level and for a longer period of time.

Application Example 2

The oxidation rate of eicosapentaenoic acid and of glycerol tris-eicosapentaenoate, respectively, was investigated using $^{14}$C-labelled eicosapentaenoic acid in an animal model in accordance with W. J. Lossow and I. L. Chaikoff (Arch. Biochem. 57:23–40, 1955).

Twenty-four male Sprague-Dawley rats (250 to 300 g) were randomly distributed into 4 groups of 6 animals each and received injections of the following fat emulsions:

Group I: Fat emulsion (20%) of highly purified fish oil
Group II: Fat emulsion (20%) of highly purified fish oil and safflower oil in a ratio of 10:10 (w.:w.)
Group III: Fat emulsion (20%) according to the preparative EXAMPLE 4 of highly purified fish oil, safflower oil and MCT oil in a ratio of 3:3:14
Group IV: Fat emulsion (20%) according to the preparative EXAMPLE 1 of highly purified fish oil and MCT oil in a ratio of 6:14 (w.:w.).

In all of the emulsions the fish oil proportion was radiolabelled by means of $^{14}$C-gycerol tris-eicosapentaenoate. The activity of the emulsions was about 6,66×10$^5$ Bq/ml (18 μCi/ml); the fat dosage rate was 2 ml/kg of body weight (≈0.4 g/kg of body weight). Immediatly after the injection, the animals were relocated into metabolism cages. The exhaled air was continuouly removed by aspiration for 6 hours and passed through an Oxifluor solution. The radioactivity retained in the Oxifluor solution as $^{14}CO_2$ was determined by a scintillation counter. The following values were found, expressed as percentage of the dose altogether administered:

Group I: 42.8±3.7
Group II: 40.3±3.9
Group III: 17.2±2.1*)
Group IV: 16.5±2.3*)
*): $p<0.001$ (vs. I and II)

In the groups III and IV, i.e. upon infusion of emulsions with concomitant MCT content, the oxidation of eicosapentaenoic acid was significantly less than in the groups I and II, in which the fish oil emulsions did not contain any medium-chain triglycerides.

Application Example 3

Eighteen male Wistar rats (300–350 g) were divided into 3 groups of 6 animals each and were infused with one of the following fat emulsions for 20 consecutive days.
Group I:
Fat emulsion (20%) comprising highly purified fish oil; dose: 22.5 ml/kg of body weight and day, corresponding to 4.5 g of fat per kg of body weight and day.
Group II:
Fat emulsion (20%) comprising highly purified fish oil and safflower oil at a ratio of 1:1 (w/w); dose: 45 ml/kg of body weight and day, corresponding to 9 g of fat per kg of body weight and day.
Group III:
Fat emulsion (20%) comprising highly purified fish oil and MCT oil at a ratio of 1:1 (w/w); dose: 45 ml/kg of body weight and day, corresponding to 9 g of fat per kg of body weight and day.

The infusions were carried out by using a catheter comprising an injection port and having been subcutaneously implanted in the neck region. The catheter was conducted subcutaneously to the jugular vein, implanted into same and advanced into the vena cava. The daily duration of infusion was 7 hours. Thirty-six hours after completion of the last infusion the animals were killed by exsanguination under ether narcosis and dissected immediately thereafter. Heart, liver, spleen, thymus, kidneys and testicles were removed, weighed and subjected to histological examination.

In Group II one died on the 16th day of infusion; in Groups I and III all of the animals survived.

The data set forth in following Table relate to the organ weights in grams (average values±SD, relative to a body weight of 1,000 g).

| Group | Heart | Liver | Spleen | Kidneys | Testicles | Thymus |
|-------|-------|-------|--------|---------|-----------|--------|
| I     | 3.2   | 43.3  | 3.6    | 4.8     | 10.5      | 1.4    |
|       | ±0.2  | ±1.6  | ±0.4   | ±0.5    | ±0.8      | ±0.2   |
| II    | 3.5   | 46.3  | 3.8    | 5.2     | 11.7      | 1.6    |
|       | ±0.3  | ±2.2  | ±0.3   | ±0.3    | ±0.6      | ±0.4   |
| III   | 3.3   | 38.6  | 2.0    | 5.1     | 11.2      | 1.3    |
|       | ±0.2  | ±1.5*)| ±0.3*) | ±0.3    | ±0.5      | ±0.2   |

*)p <0.05; Group III vs. Groups I and II, respectively.

Figure 2A:
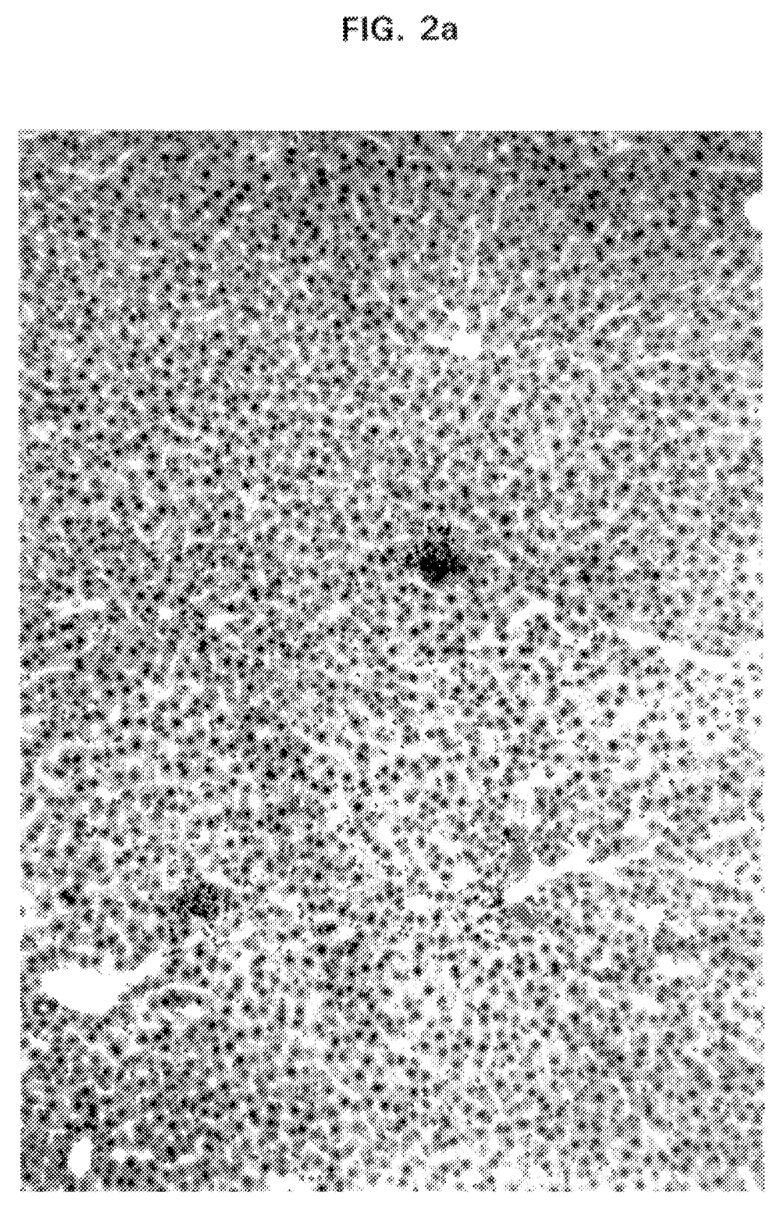
FIG. 2a shows the storage of neutral lipid in Kupffer cells of the liver of test animals.
Figure 2B:
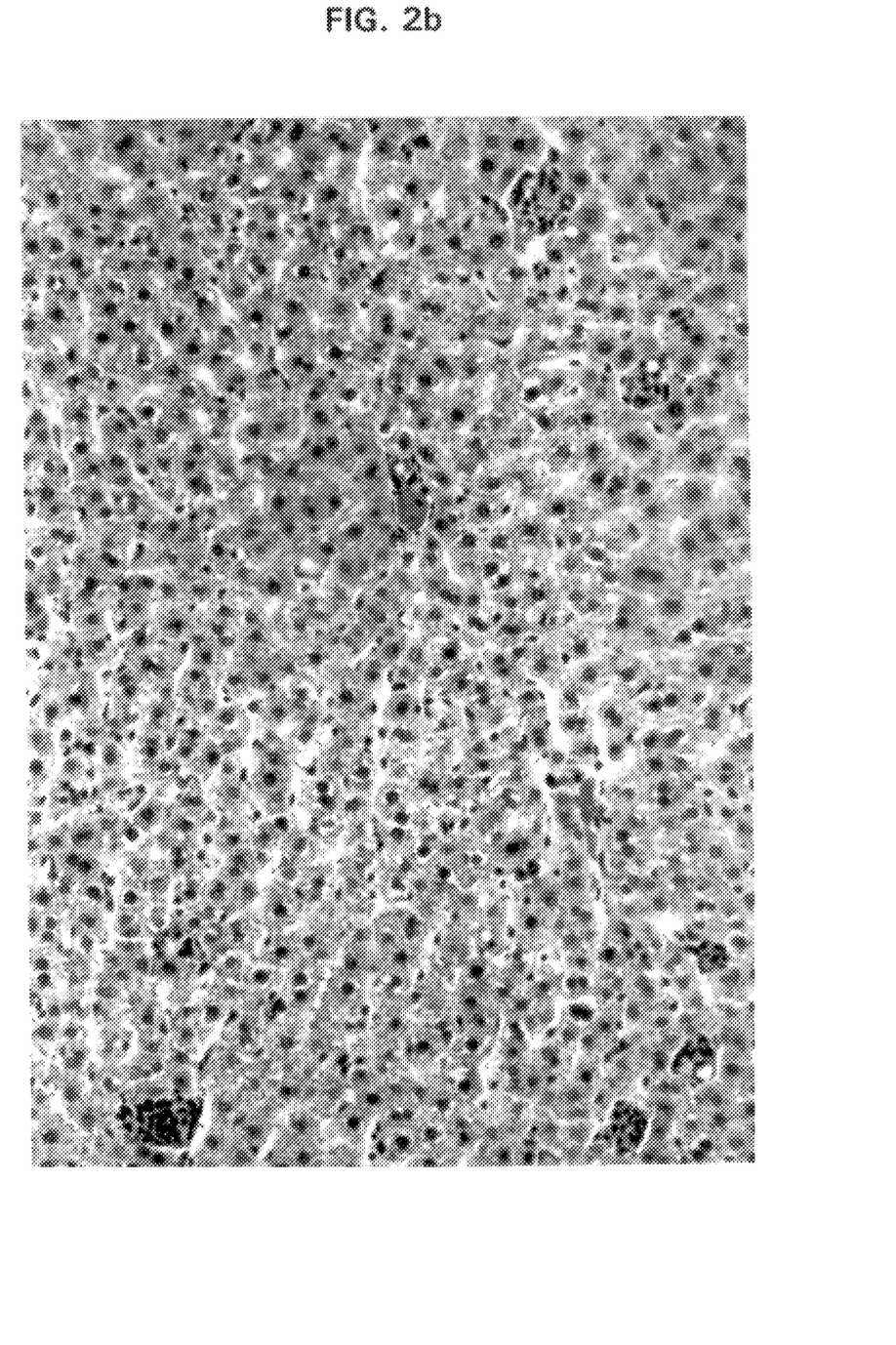
FIG. 2b shows the formation of Kupffer's star cells.
Figure 2C:
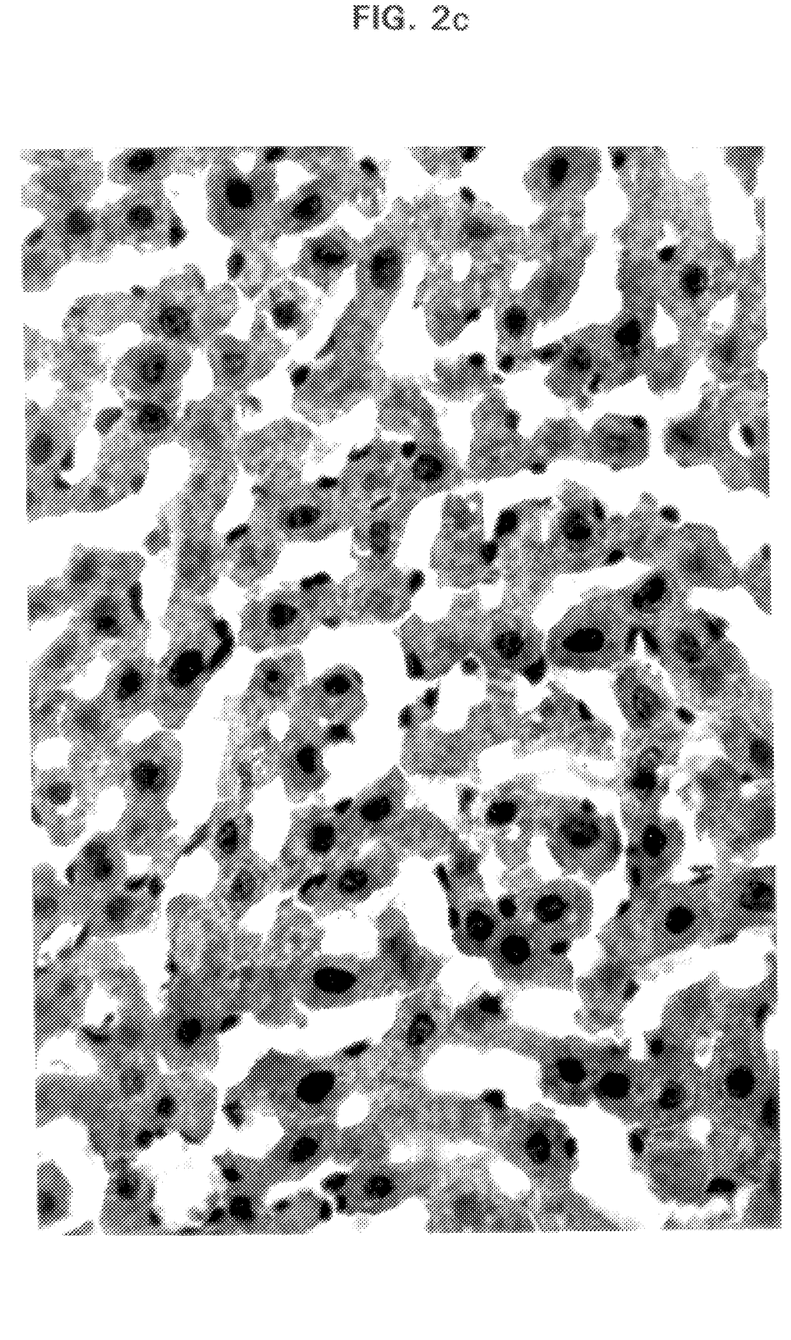
FIG. 2c shows the lack of formation of Kupffer's star cells.

According to the above Table, Group III which had been administered an emulsion comprising fish oil and MCT oil exhibited significantly lower weights of liver and spleen than in Groups I (administration of an emulsion of only fish oil) and II (fish oil and safflower oil processed to give a combined emulsion). Normal liver findings corresponded to the lower liver weight of Group III, whereas in Groups I and II a storage of neutral lipid was detectable in Kupffer cells of the liver with formation of star cell nodules and a storage of neutral lipid in the parenchymal cells, as is apparent from FIG. 2.

We claim:

1. An isotonic fat emulsion for parenteral administration comprising:

at least one ω-3-fatty acid, said ω-3-fatty acid being essentially eicosapentaenoic acid, present as a component of marine oil derived from processing cold water fish, medium chain triglycerides comprising at least 90% caprylic and/or capric acid triglycerides by weight, at least one physiologically acceptable emulsifier, and at least one ω-6-fatty acid said ω-6-fatty acid being essentially linoleic acid, present as a component of soybean and/or safflower oil, at a content of 10% to 30% by weight of total lipid, the ratio of said ω-3-fatty acid to said medium chain triglycerides being between 1:9 and 3:5 by weight, the total fat content being between 5% and 30% by weight of said emulsion, and the emulsifier content being between 5% and 12% based on the weight of said fat content.

2. The fat emulsion according to claim 1 containing in addition an antioxidant to protect against peroxide formation selected from the group consisting of α-tocopherol and physiologically acceptable esters of α-tocopherol, said antioxidant being in an amount from 10 to 1000 mg per 100 g of fat content.

3. The fat emulsion according to claims 1 or 2 in which said emulsifier comprises a phospholipid of animal or vegetable origin or a mixture of said phospholipid with sodium salts of long-chain fatty acids or cholesterol or cholesterol esters, and said emulsion has a pH from 6 to 9.

* * * * *

UNITED STATES PATENT AND TRADEMARK OFFICE
CERTIFICATE OF CORRECTION

PATENT NO. : 5,874,470
DATED : February 23, 1999
INVENTOR(S) : Joerg Nehne; Michael Boll It is certified that error appears in the above-identified patent and that said Letters Patent is hereby corrected as shown below:

Column 1, line 9, replace "U.S. Ser. No. 07/559,399filed Jul. 26, 1990"
    with -- U.S. Ser. No. 07/559,399, filed Jul. 26, 1990 --.
Column 1, line 11, change "Oct. 6, 1998" to -- Oct. 6, 1988 --.
Column 5, line 15, change "an other" to another --.
Column 6, line 25, change "-3-fatty acids" to -- ω-3-fatty acids --.
Column 7, line 31, change "contents" to -- content --.
Column 10, line 52, change "Immediatly" to -- Immediately --.

Signed and Sealed this

Thirtieth Day of May, 2000

Attest:

Q. TODD DICKINSON

Attesting Officer     Director of Patents and Trademarks